United States Patent [19]

Wittkampf

[11] Patent Number: 5,741,310

[45] Date of Patent: Apr. 21, 1998

[54] SYSTEM AND METHOD FOR HEMODYNAMIC PACING IN VENTRICULAR TACHYCARDIA

[75] Inventor: Frederik H. M. Wittkampf, Bilthoven, Netherlands

[73] Assignee: Medtronic, Inc., Minneapolis, Minn.

[21] Appl. No.: 548,541

[22] Filed: Oct. 26, 1995

[51] Int. Cl.$^6$ .............................. A61N 1/365; A61N 1/37
[52] U.S. Cl. .................... 607/14; 607/9; 607/13
[58] Field of Search ........................ 607/13, 14, 9

[56] References Cited

U.S. PATENT DOCUMENTS

| | | | |
|---|---|---|---|
| 3,857,399 | 12/1974 | Zacouto | 607/9 |
| 4,280,502 | 7/1981 | Baker, Jr. et al. | 607/14 |
| 4,452,248 | 6/1984 | Keller, Jr. | 607/9 |
| 4,488,554 | 12/1984 | Nappholz et al. | 607/14 |
| 4,593,695 | 6/1986 | Wittkampf | 607/14 |
| 5,312,451 | 5/1994 | Limousin et al. | 607/15 |
| 5,549,650 | 8/1996 | Bornzin et al. | 607/24 |

OTHER PUBLICATIONS

Technical Note: "A Triggered Generator For the Electrical Treatment of Tachycardias," Med. & Biol. Eng., 10, pp. 297–300, Pergamon, 1972.

Primary Examiner—William E. Kamm
Assistant Examiner—Carl H. Layno
Attorney, Agent, or Firm—Michael J. Jaro; Harold Patton

[57] ABSTRACT

A system and method for providing a 1:2 pacing therapy in response to a sensed ventricular tachycardia, which results in an improved hemodynamic response while limiting the potential for interrupting the tachycardia in a way that can cause a more dangerous tachycardia, or even VF. The pacing therapy involves obtaining a measure of the time interval between ventricular beats, and using this information to time out and deliver alternate stimulus pulses which occur just a short time interval ($\Delta$) before the next expected natural ventricular beat. By delivering the alternate cycle stimulus at a predetermined time interval before the expected ventricular beat, the advantage of increased arterial pressure on alternate spontaneous beats is obtained, while avoiding the danger of evoking a more dangerous arrhythmia. The system further monitors change in rate while therapy is being applied, and either adjusts the timing or exits the routine whenever significant rate change is detected.

23 Claims, 2 Drawing Sheets

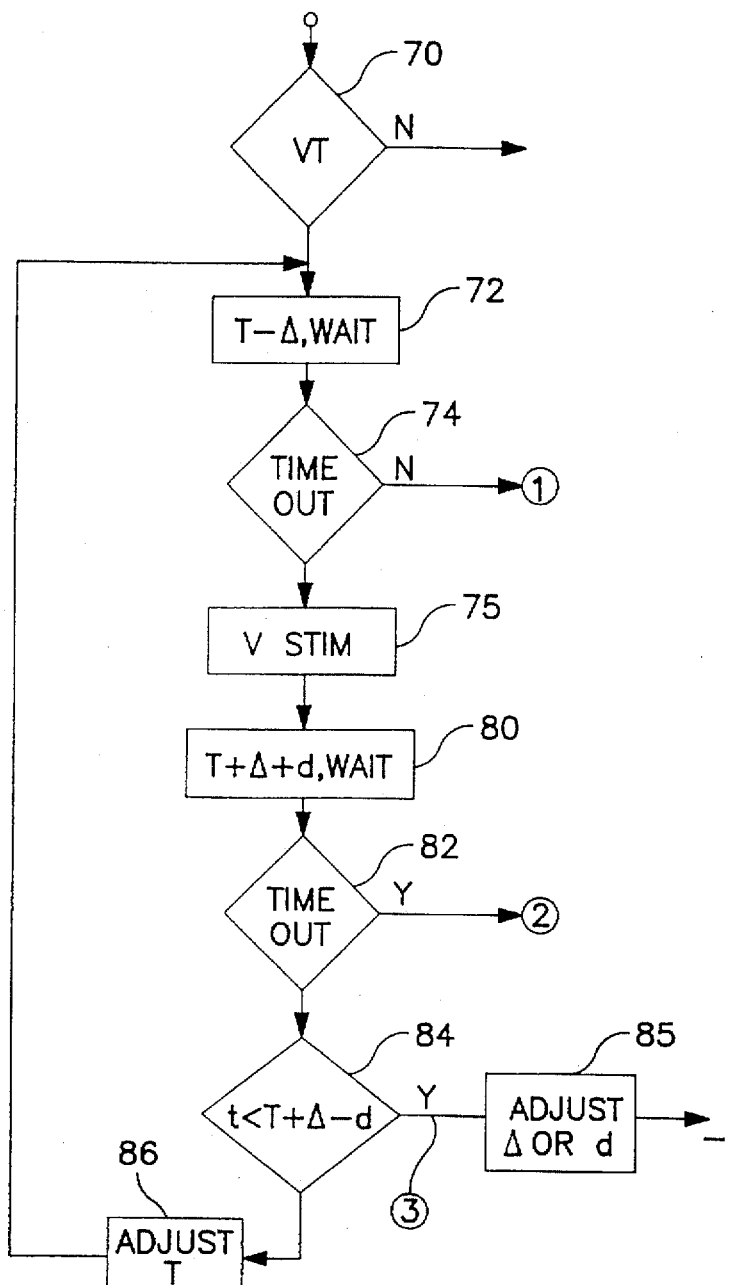
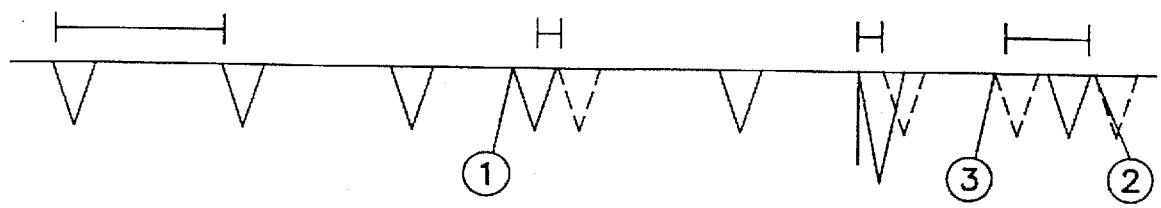
FIG. 3
FIG. 4

SYSTEM AND METHOD FOR HEMODYNAMIC PACING IN VENTRICULAR TACHYCARDIA

BACKGROUND OF THE INVENTION

This invention relates to a pacing therapy for controlling the effect of ventricular tachycardia (VT) and, more particularly, a system and method for delivering a specific pacing therapy when VT is detected.

Ventricular tachycardia is a subject that has been widely investigated, and different therapies have been proposed. It is known in the art to provide specific pacing therapies for trying to control or suppress VT. Such pacing therapy is preferably applied by a device which includes an automatic defibrillator and a pacemaker, so that back-up therapies are available. While certain therapies have been noted to achieve a certain success in controlling VT, it remains an area where significant improvement is desired. Uncontrolled VT can, as is known, lead to ventricular fibrillation (VF), which even when treated imposes a serious trauma and consequence on the patient.

In another environment, namely a catheterization lab, there occurs a circumstance of investigating the focus of a patient tachycardia, usually in the left ventricle. In this circumstance, it is actually desirable not to suppress the tachycardia, since the VT should be maintained in order to complete the investigation. However, it is also very desirable to improve cardiac output so that the patient can tolerate the procedure. There is thus an additional need to provide a therapy applicable in this circumstance, to enhance the patient condition during VT and prevent the patient from slipping into VF.

It has been observed that in some patients with VT or supraventricular VT, the arterial pressure waves often show a 1:2 ratio with the underlying electrical rhythm of the heart. This situation occurs spontaneously in some patients, and the hemodynamic response to stable VT may vary between a 1:1 and a 1:2 response, with a relatively slow and gradual alternation between these responses. This can be observed during electrophysiological studies when arterial pressure is monitored together with the ECG. It is also possible that a 1:2 response can be induced by a single extra stimulus that is delivered, as during electrophysiological studies. Such a 1:2 hemodynamic response which is induced in this way often disappears gradually within five to ten beats after initiation. Of importance is the observation that such alternating arterial pressure waves may provide significant increase in cardiac output, and relief to the patient, even though the VT continues.

In 1972 Imich and coworkers described a 1:2 pacing algorithm in patients with various tachyrhythmias. See "A Triggered Generator For the Electrical Treatment of Tachycardias," Med. and Biol. Eng. 10, pp. 297-300, Pergamon Press, 1972. Single extra stimuli with short coupling intervals, i.e., short intervals following the last tachy beat, were delivered to induce alternating arterial pressure waves. The short interval results in a decreased filling of the ventricles and low systolic pressure, while the longer duration of the next diastolic interval that follows causes an increased end-diastolic volume and a higher end-systolic pressure. The coupling disclosed in the referenced paper is relatively short, in the range of about 150 to 250 ms. In fact, the purpose was to deliver the extra stimulus as early as possible after the termination of the ventricular refractory period. However, pacing with very short coupling intervals relative to the preceding spontaneous beats has the potential to change the tachycardia in a dangerous manner. While the referenced paper reports that the extra stimulus sometimes terminated the tachycardia, it also has the potential to change the tachycardia into another and more dangerous type. It is my observation that any therapy which seeks to realize the benefit of 1:2 pacing must be programmed to avoid interrupting the tachycardia; anti-tachyrhythmia pacing, due to its potential for danger, should only be undertaken in conjunction with a defibrillator, and in any event not in an implantable pacemaker with no defibrillation backup. There thus is a need to provide a safer, and yet efficient pacing therapy, with a reduced potential to change the tachycardia into a more dangerous type and otherwise distort the recovery from tachycardia.

It is my observation that very short coupling intervals are not necessary to obtain a hemodynamic 1:2 response. Specifically, it is my observation that only slight variations in cycle length are required to induce the benefit of 1:2 pacing, namely increasing amplitude of alternate arterial pressure waves. Since most VTs have a circuit or focus that is located in the left ventricle, and since the pacing stimulating electrode is positioned in the right ventricle, the distance from the electrode to the source of tachycardia is relatively large. This means that a stimulus that is delivered shortly before the expected spontaneously occurring depolarization will not interfere with the VT mechanism.

Accordingly, the basis of the subject invention is to provide 1:2 pacing as a response to VT, with a timing of the alternate stimulus being such that every second beat is advanced only slightly, preferably on the order of 40-60 ms relative to the expected timing of the next beat. A stimulus delivered less than 30 seconds before the expected next beat would have no effect; and a stimulus more than about 125-150 ms early could be dangerous. The timing of the stimulus should be adjusted to the cycle length of the tachycardia, so that the advancement (Δ) is a time interval independent of the tachy rate. By coupling the stimulus to the next expected next beat, as opposed to the last beat, and keeping the advancement relatively small, the benefit of the therapy is obtained without risking interruption of the tachycardia.

SUMMARY OF THE INVENTION

It is an object of this invention to provide a system and method for providing a hemodynamic pacing therapy in response to ventricular tachycardia, the therapy giving the benefit of increased arterial pressure while avoiding the danger of invoking a more dangerous form of VT, or VF. This object is met by controlling the delivery of a stimulus pulse every second beat during stable VT, the stimulus pulse being timed in relation to the next expected natural beat, and preceding such next expected natural beat by only a short time duration which is in the range of 30-150 ms. The system and method provide for monitoring changes in the VT rate during the 1:2 pacing, and for adjusting the timing or exiting the pacing therapy when certain differences in the natural rate are detected, i.e., the tachy is not stable. The pacing therapy of this invention provides an improved hemodynamic performance during VT, which in turn enables a longer period of relative comfort for the patient, and which results in reduction in the number of VF episodes. The improved hemodynamic performance enables a longer period during which alternate anti-tachycardia pacing attempts can be attempted under appropriate circumstances, and is of great benefit to the patient during procedures such as catheter mapping.

BRIEF DESCRIPTION OF THE DRAWINGS

FIG. 3 is a flow diagram showing the primary sequential steps carried out cyclically by the pacemaker of this invention, limited to the steps taken in performing the 1:2 pacing during VT, in accordance with this invention.

FIG. 4 is a timing diagram which illustrates the operation of the pacing algorithm of this invention during a condition of ventricular tachycardia.

DESCRIPTION OF THE PREFERRED EMBODIMENTS

The system of this invention is based upon a device capable of providing a specific pacing therapy in response to VT. Although the system is illustrated in terms of a pacemaker which provides a pacing response, it is noted that such a pacemaker is preferably incorporated as part of a larger system capable of delivering defibrillation therapy in the event that the patient goes into ventricular fibrillation. Also, it may be combined with a system that can be programmed to provide an alternate form of anti-tachycardia therapy.

Figure 1:
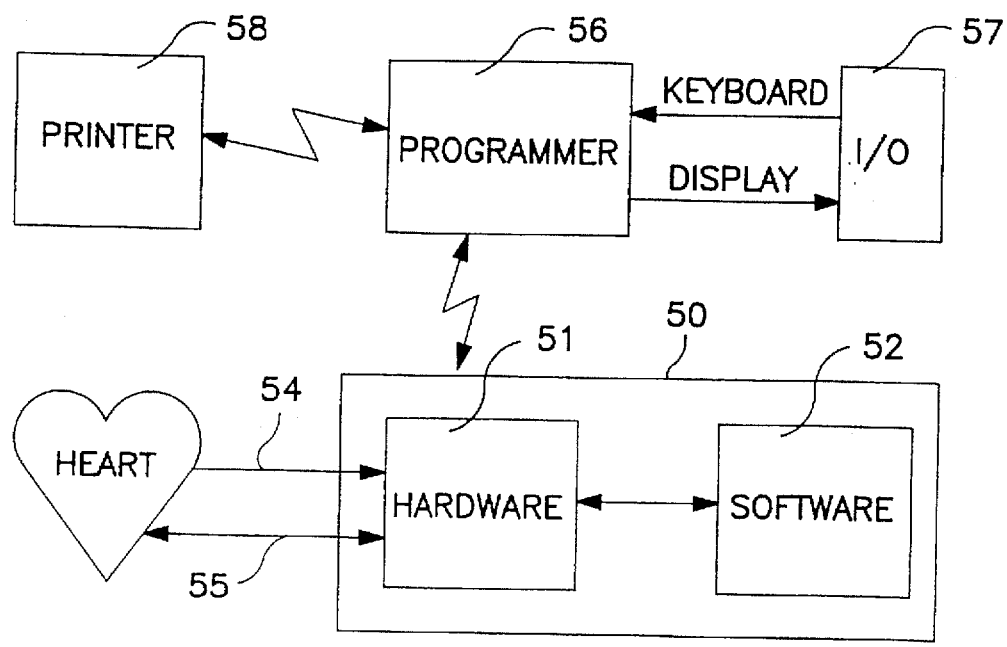
FIG. 1 is a block diagram of the overall system of the invention, showing the environment in which the pacemaker operates.

The system of this invention is preferably software-based, i.e., the software controls functions through hardware, as illustrated in FIG. 1. Referring specifically to FIG. 1, the pacemaker portion 50 of the device of this invention is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode, unipole or bipole, positioned in the heart. The line 54 is illustrated as leading to the heart, as in a QT-type sensor arrangement, but may be attached to the outside case of the pacemaker or may couple to any other available sensors for sensing body parameter information used in rate responsive pacing systems.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
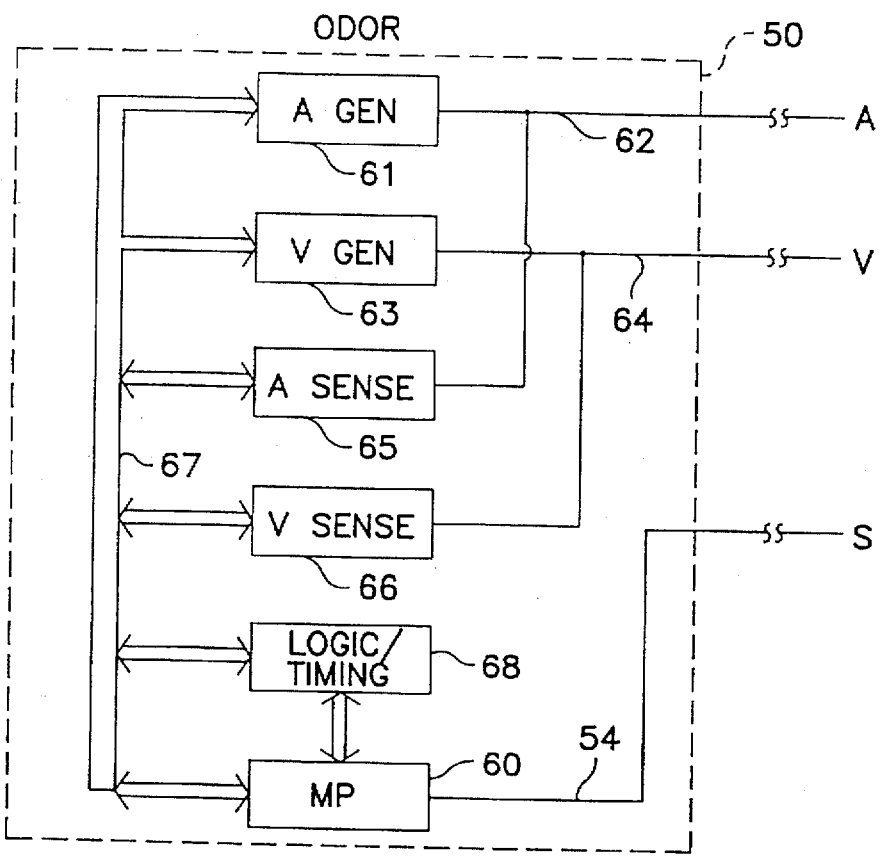
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of a DDDR pacer 50. Although the subject invention is limited to ventricular pacing, a dual chamber DDDR pacer is illustrated, since the invention could be practiced with a single chamber pacemaker portion, or a programmable dual chamber portion. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function, and specifically setting the ventricular escape interval ($V_{esc}$), is well known in the art, such that the following detailed discussions of a preferred software routine enables one of ordinary skill in this art area to design a system for carrying out the functions within the scope of the invention. Data inputted from programmer 56 is stored in memory associated with microprocessor. A sensor S may also be used for providing rate information if the device is to be used as a rate responsive pacemaker.

Referring now to FIG. 3, there is shown a flow diagram which is limited to illustrating the primary steps taken cyclically by a pacemaker incorporating the features of this invention, in order to set $V_{esc}$ so as to control ventricular pacing during VT. The routine is preferably run under the control of microprocessor 60. At block 70, a determination is made as to whether or not there is a condition of ventricular tachycardia (VT). Techniques for determining VT are well known in the art, and the criteria for detecting onset of tachycardia can be programmed by one of ordinary skill in the art utilizing a conventional programmer as illustrated at 56 in FIG. 1. The determination of VT includes getting a measure of T, the tachycardia cycle length. If it is determined that there is no VT, the device can be programmed to remain quiescent, i.e., deliver no pace pulses until a VT is detected. Alternately, the device can act as a conventional pacemaker, in which case handling of the ventricular event is done in the conventional manner. Thus, when the patient is without VT, the pacer sets $V_{esc}$ and waits to see whether it times out or whether a $V_{sense}$ intervenes. When there has been a time out, the pacemaker delivers a ventricular pace pulse (VP) and resets $V_{esc}$; if a $V_{sense}$ has been determined, no VP is delivered, and the pacemaker simply resets $V_{esc}$.

Returning to block 70, if VT has been detected, the routine proceeds to block 72, and sets $V_{esc}$ to the value of T−Δ, where Δ is a programmed constant and reflects the advance before the next expected tachy beat when a pulse is to be delivered early. In other words, for a tachy with a substantially constant T, every other cycle the pacer will try to deliver a stimulus pulse at a time Δ before the tachy beat would otherwise occur. After $V_{esc}$ is set, the pacemaker waits to see if it times out, or whether time out is preceded by a sensed ventricular beat, $V_{sense}$. At 74, the next event is examined to see if it was a time out. If no, this means that there was a $V_{sense}$ before time out, as seen at (1) in FIG. 4. In this event, the routine exits, since the tachy is not stable enough for effective 1:2 pacing therapy. However, if the event was a time out, the pacemaker delivers a V stimulus, as seen at block 75.

Following delivery of a stimulus, the routine resets $V_{esc}$, as seen at block 80. The $V_{esc}$ is set to a value of T+Δ+d, where d is a predetermined value representative of the maximum tolerated variation in T. The pacemaker then waits for the next event. Upon occurrence of the next event, it is determined at 82 whether there has been a time out of the escape interval. If yes, this means that no sense has been detected, such that the next sense is going to be after T+Δ+d, as illustrated at (2) in FIG. 4. This indicates that the tachy is slowing down, and it is preferable not to deliver a stimulus pulse. Accordingly, the routine exits. However, if there has not been a time out, the routine goes to 84 and determines whether the sense has occurred before T+Δ–d, as illustrated at (3) in FIG. 4. If yes, the tachy has increased, or accelerated, and it is preferred not to remain in this 1:2 routine. The pacemaker can adjust the routine, such as by varying Δ or d, as shown at 85, or just exit the routine. However, if the answer at 84 is no, the routine goes to block 86 and updates the value of T. This is preferably done by timing the period between $V_{sense}$ events, i.e., senses before and after a V stimulus, and dividing by 2. The routine then loops back to 72, and sets the escape interval to deliver a next early pace pulse.

It is seen that for a substantially stable VT, the routine of FIG. 3 provides delivery of a pace pulse every other cycle, or 1:2 pacing; each delivered pulse is advanced in time relative to the expected next natural ventricular beat, giving rise to the beneficial increasing arterial pressure. At the same time, this pacing mode is not continued if either a rapidly increasing or decreasing VT is detected, i.e., the tachy is not substantially stable. By timing the 1:2 pacing with respect to the next expected beat, and limiting the A advance to about 30–150 ms, and preferably 30–90 ms, the pacing does not interrupt the tachycardia, but it improves the hemodynamic performance and lessens the likelihood of ventricular fibrillation.

What is claimed is:

1. An implantable cardiac pacing system, having a controllable pulse generator for generating pacing pulses and a lead for delivering pacing pulses to a patient's ventricle and for sensing natural heartbeats in said patient's ventricle, VT means for detecting when said patient is in ventricular tachycardia, response means for responding to detected VT by controlling said pulse generator to deliver pace pulses in a 1:2 relation to the patient's natural cardiac rhythm during said VT, said response means having:

measure means for determining a measure of the patient's natural rhythmic interval (T) during said VT;

determining means operative after a sensed natural heartbeat for determining, based on said measure of T, a time of expected occurrence of the patient's next natural heartbeat; and control means for controlling said pulse generator to generate a pacing pulse following a ventricular sense and before the said next expected natural heartbeat, said pacing pulse to precede said next expected heartbeat by a predetermined time greater than 30 ms and less than 150 ms.

2. The pacing system as described in claim 1, wherein said predetermined time is in the range of 40–60 ms.

3. The pacing system as described in claim 1, wherein said predetermined time is greater than 50 ms.

4. The pacing system as described in claim 1, wherein said measure means comprises means for determining the time interval between the natural beat preceding a delivered pacing pulse and the natural beat following said delivered pacing pulse.

5. The pacing system as described in claim 1, comprising means for adjusting said predetermined time.

6. The pacing system as described in claim 1, comprising tachy change means for determining when the patient VT has changed by more than a predetermined tolerance, and adjust means for adjusting the response of said response means when VT is determined to have changed by more than said tolerance.

7. A device for treatment of cardiac arrhythmias, said device having a controllable pulse generator for generating stimulus pulses, lead means for delivering stimulus pulses to a patient's heart, sense means connected to said lead means for sensing ventricular beats, tachy means for determining when the patient is in VT, and 1:2 response means for responding to VT, said 1:2 response means having timing means for timing out an early escape interval following a sensed ventricular beat, said timing means having determining means for determining the time of the next expected ventricular beat, and escape interval means for setting an escape interval calculated to time out a predetermined Δ interval before said time of the next expected beat, and control means for controlling said pulse generator to deliver an early stimulus pulse at the time out of said early escape interval in the absence of an intervening ventricular beat.

8. The device as described in claim 7, comprising tachy change means for determining when the patient VT changes by more than a predetermined tolerance, and wherein said 1:2 response means has disable means for disabling said 1:2 response means when there is a said determined VT change.

9. The device as described in claim 7, comprising tachy change means for determining when the patient VT changes by more than a predetermined tolerance, and comprising response adjust means for adjusting said response when there is a said predetermined VT change.

10. The device as described in claim 7, comprising Δ change means for changing said predetermined Δ.

11. The device as described in claim 7, wherein said determining means comprises means for determining a running measure of the time interval corresponding to the rate of natural ventricular beats during VT.

12. The device as described in claim 7, comprising means for setting said Δ at a value in the range of 30–150 ms.

13. The device as described in claim 11, wherein said control means further comprises means operative after delivery of a said early stimulus pulse for controlling said pulse generator to time out an escape interval which is greater than said time interval measure by at least said Δ.

14. A method of responding to an episode of ventricular tachycardia (VT) in a patient, comprising sensing the occurrence of a ventricular beats, determining a measure of the beat to beat interval of said VT, following a sensed ventricular beat, calculating an early escape interval which is less than said beat to beat interval by Δ amount, where said Δ amount is in the range of 30–150 ms, and initiating time out of said escape interval following said sensed beat, and delivering an early stimulus pulse to the patient when said early escape interval times out without an intervening patient heartbeat further comprising limiting said Δ to 30–90 ms.

15. The method as described in claim 14, comprising determining when the rate of the patient's VT changes by more than a predetermined tolerance, and adjusting the response to VT as a function of said determining.

16. A method of responding to an episode of ventricular tachycardia (VT) in a patient, comprising sensing the occurrence of a ventricular beats, determining a measure of the beat to beat interval of said VT, following a sensed ventricular beat, calculating an early escape interval which is less than said beat to beat interval by a Δ amount, where said Δ amount is in the range of 30–150 ms, and initiating time out of said escape interval following said sensed beat, and delivering an early stimulus pulse to the patient when said early escape interval times out without an intervening patient heartbeat further comprising determining when the patient VT is not stable, and terminating said responding when VT is determined not to be stable.

17. A method of responding to an episode of ventricular tachycardia (VT) in a patient, comprising sensing the occurrence of a ventricular beats, determining a measure of the beat to beat interval of said VT, following a sensed ventricular beat, calculating an early escape interval which is less than said beat to beat interval by a Δ amount, where said Δ amount is in the range of 30–150 ms, and initiating time out of said escape interval following said sensed beat, and delivering an early stimulus pulse to the patient when said early escape interval times out without an intervening patient heartbeat further comprising following delivery of a said early stimulus pulse, timing out an escape interval greater than said beat-to-beat interval by at least said amount.

18. An implantable cardiac pacing system, comprising:

a controllable pulse generator for generating pacing pulses;

a lead for delivering pacing pulses to a patient's ventricle and for sensing natural heartbeats in the patient's ventricle, VT means for detecting when the patient's heart is in VT; and means for providing improved hemodynamic performance during VT in response to the detected VT through the deliver of a hemodynamic pacing therapy.

19. The pacing system as described in claim 18, wherein means for providing improved hemodynamic performance during VT in response to the detected VT through the deliver of a hemodynamic pacing therapy comprises means for responding to detected VT by controlling the pulse generator to deliver pace pulses in a 1:2 relation to the patient's natural cardiac rhythm during the VT, the means for responding to detected VT having:

measure means for determining a measure of the patient's natural rhythmic interval (T) during the VT;

determining means operative after a sensed natural heartbeat for determining, based on the measure of T, a time of expected occurrence of the patient's next natural heartbeat; and control means for controlling the pulse generator to generate a pacing pulse following a ventricular sense and before the next expected natural heartbeat, the pacing pulse to precede the next expected heartbeat by a predetermined time greater than 30 ms and less than 150 ms.

20. The pacing system as described in claim 18, wherein the predetermined time comprises the range of 40–60 ms.

21. The pacing system as described in claim 18, wherein the predetermined time comprises a period greater than 50 ms.

22. The pacing system as described in claim 19, wherein the measure means comprises means for determining time interval between the natural beat preceding a delivered pacing pulse and the natural beat following the delivered pacing pulse.

23. The pacing system as described in claim 19, comprising means for adjusting the predetermined time.

* * * * *